(12) United States Patent
Stedman

(10) Patent No.: US 8,347,701 B2
(45) Date of Patent: Jan. 8, 2013

(54) SYSTEM AND METHOD FOR QUANTIFYING THE PRESENCE OF COMPONENTS IN THE EXHAUST OF COMMERCIAL AND/OR HEAVY-DUTY VEHICLES

(75) Inventor: Donald H. Stedman, Denver, CO (US)

(73) Assignee: Envirotest Systems Holdings Corp., East Granby, CT (US)

( * ) Notice: Subject to any disclaimer, the term of this patent is extended or adjusted under 35 U.S.C. 154(b) by 10 days.

(21) Appl. No.: 13/153,151

(22) Filed: Jun. 3, 2011

(65) Prior Publication Data

US 2011/0265552 A1 Nov. 3, 2011

Related U.S. Application Data

(63) Continuation-in-part of application No. 13/052,815, filed on Mar. 21, 2011, now Pat. No. 8,266,952, which is a continuation of application No. 12/114,189, filed on May 2, 2008, now Pat. No. 7,930,931.

(51) Int. Cl.
*G01N 33/00* (2006.01)
(52) U.S. Cl. .................... 73/114.71; 73/23.31
(58) Field of Classification Search ............... 73/23.31, 73/23.33, 114.71
See application file for complete search history.

(56) References Cited

U.S. PATENT DOCUMENTS

| | | | |
|---|---|---|---|
| 2,658,434 A | 11/1953 | Miller | |
| 2,726,594 A | 12/1955 | Cooper et al. | |
| 3,439,527 A | 4/1969 | Rohrer | |
| 4,216,710 A | 8/1980 | Asmus | |
| 4,704,897 A | 11/1987 | Kawase et al. | |
| 4,924,095 A | 5/1990 | Swanson, Jr. | |
| 4,979,390 A | 12/1990 | Schupack et al. | |
| 5,046,353 A | 9/1991 | Thompson | |
| 5,167,146 A | 12/1992 | Hostetter | |
| 5,210,702 A | 5/1993 | Bishop et al. | |
| 5,252,828 A | 10/1993 | Kert et al. | |
| 5,291,265 A | 3/1994 | Kebabian | |
| 5,319,199 A | 6/1994 | Stedman et al. | |
| 5,343,043 A | 8/1994 | Johnson | |
| 5,369,976 A | 12/1994 | Ratton | |
| 5,371,367 A | 12/1994 | DiDomenico et al. | |
| 5,388,453 A | 2/1995 | Ratton et al. | |

(Continued)

FOREIGN PATENT DOCUMENTS

EP 0 681 179 A1 11/1995

(Continued)

OTHER PUBLICATIONS

Zahniser, Mark S., et al., "Measurement of Trace Gas Fluxes Using Tunable Diode Laser Spectroscopy", *Phil. Trans. R. Soc. Lond. A*, vol. 351, 1995, pp. 371-382.

(Continued)

*Primary Examiner* — Freddie Kirkland, III
(74) *Attorney, Agent, or Firm* — Pillsbury Winthrop Shaw Pittman LLP

(57) ABSTRACT

A system and/or method for quantifying the presence of one or more components in vehicle exhaust, and more particularly to a non-contact, sampling system and method for quantifying the presence of one or more components in exhaust emissions of commercial and/or heavy-duty vehicles that emit exhaust at an elevated level, under actual operating conditions.

25 Claims, 5 Drawing Sheets

U.S. PATENT DOCUMENTS

| | | | |
|---|---|---|---|
| 5,401,967 A | 3/1995 | Stedman et al. |
| 5,414,626 A | 5/1995 | Boorse et al. |
| 5,418,366 A | 5/1995 | Rubin et al. |
| 5,469,731 A | 11/1995 | Decker et al. |
| 5,488,875 A | 2/1996 | Adair |
| 5,489,777 A | 2/1996 | Stedman et al. |
| 5,498,872 A | 3/1996 | Stedman et al. |
| 5,583,765 A | 12/1996 | Kleehammer |
| 5,589,629 A | 12/1996 | Quinn |
| 5,591,975 A | 1/1997 | Jack et al. |
| 5,644,133 A | 7/1997 | Didomenico et al. |
| 5,693,872 A | 12/1997 | Quinn |
| 5,719,396 A | 2/1998 | Jack et al. |
| 5,726,450 A | 3/1998 | Peterson et al. |
| 5,797,682 A | 8/1998 | Kert et al. |
| 5,831,267 A | 11/1998 | Jack et al. |
| 5,877,862 A | 3/1999 | Nelson et al. |
| 6,025,920 A | 2/2000 | Dec |
| 6,306,031 B1 | 10/2001 | Hansen et al. |
| 6,307,201 B1 | 10/2001 | Didomenico et al. |
| 6,455,851 B1 | 9/2002 | Lord et al. |
| 6,560,545 B2 | 5/2003 | Stedman et al. |
| 6,671,630 B2 | 12/2003 | Stedman et al. |
| 6,701,256 B2 | 3/2004 | Stedman et al. |
| 6,723,989 B1 | 4/2004 | Didomenico et al. |
| 6,983,639 B1 | 1/2006 | DiDomenico et al. |
| 7,049,595 B2 | 5/2006 | Kansakoski et al. |
| 7,071,002 B1 | 7/2006 | Tefft et al. |
| 7,131,319 B2 | 11/2006 | Ganassi et al. |
| 7,164,132 B2 | 1/2007 | Didomenico et al. |
| 7,275,414 B2 | 10/2007 | Nelson, Jr. et al. |
| 7,305,870 B2 | 12/2007 | Ganassi et al. |
| 7,930,931 B2 * | 4/2011 | Stedman ............. 73/114.71 |
| 8,266,952 B2 * | 9/2012 | Stedman ............. 73/114.71 |
| 2002/0052698 A1 | 5/2002 | Didomenico et al. |
| 2002/0194897 A1 | 12/2002 | Arnott et al. |
| 2003/0089854 A1 | 5/2003 | Shifflett et al. |
| 2003/0120434 A1 | 6/2003 | DiDomenico et al. |
| 2003/0136177 A1 | 7/2003 | Hendren et al. .......... 73/23.31 |
| 2004/0155191 A1 | 8/2004 | Stedman et al. |
| 2006/0096394 A1 | 5/2006 | Nelson, Jr. et al. |
| 2006/0108221 A1 | 5/2006 | Goodwin et al. .......... 204/424 |
| 2007/0209544 A1 | 9/2007 | Caro et al. |
| 2009/0272181 A1 | 11/2009 | Stedman ............. 73/114.71 |
| 2011/0162435 A1 | 7/2011 | Stedman |

FOREIGN PATENT DOCUMENTS

| | | |
|---|---|---|
| WO | WO 92/12411 | 7/1992 |
| WO | WO 98/37405 | 8/1998 |
| WO | WO 02/082059 | 10/2002 |

OTHER PUBLICATIONS

Nelson, David D., et al., "High Precision Measurements of Atmospheric Nitrous Oxide and Methane Using Thermoelectrically Cooled Mid-Infrared Quantum Cascade Lasers and Detectors", *Spectrochimica Acta Part A*, 2004, pp. 1-11.

Houghton, J. T., et al., "Climate Change 2001: The Scientific Basis", Contribution of Working Group I to the Third Assessment Report of the Intergovernmental Panel of Climate Change, First published 2001, pp. i-x.

The North American Carbon Program, NACP Committee of the U.S. Carbon Cycle Science Steering Group, 2002, pp. ii-v.

Nelson, D. D., et al., "Sub-Part-Per-Billion Detection of Nitric Oxide in Air Using a Thermoelectrically Cooled Mid-Infrared Quantum Cascade Laser Spectrometer", *Applied Physics B*, vol. 75, 2002, pp. 343-350.

Edwards, G. C., et al., "Eddy Correlation Measurements of Methane Fluxes Using a Tunable Diode Laser at the Kinosheo Lake Tower Site During the Northern Wetlands Study (NOWES)", *Journal of Geophysical Research*, vol. 99, No. D1, Jan. 20, 1994, pp. 1511-1517.

Wienhold, F. G., et al., "Measurements of $N_2O$ Fluxes from Fertilized Grassland Using a Fast Response Tunable Diode Laser Spectrometer", *Journal of Geophysical Research*, vol. 99, No. D8, Aug. 20, 1994, pp. 16,557-16,567.

Kosterev: Anatoliy A., et al., "Transportable Automated Ammonia Sensor Based on a Pulsed Thermoelectrically Cooled Quantum-Cascade Distributed Feedback Laser", *Applied Optics*, vol. 41, No. 3, Jan. 20, 2002, pp. 573-578.

Allan, David W., "Statistics of Afornic Frequency Standards", *Proceedings of the IEEE*, vol. 54, No. 2, Feb. 1966, pp. 221-230.

Hansen, James, et al., "Global Warming in the Twenty-First Century: An Alternative Scenario", *PNAS*, vol. 97, No. 18, Aug. 29, 2000, pp. 9875-9880.

Kormann, Robert, et al., "Eddy Flux Measurements of Methane Over the Fen 'Murnauer Moos', 11°11'E, 47°39'N, Using a Fast Tunable Diode Laser Spectrometer", *Atmospheric Environment*, vol. 35, 2001, pp. 2533-2544.

Werle, Peter, et al., "Fast Chemical Sensor for Eddy-Correlation Measurements of Methane Emissions from Rice Paddy Fields", *Applied Optics*, vol. 40, No. 6, Feb. 20, 2001, pp. 846-858.

McManus, J. Barry, et al., "Quantum Cascade Lasers for Open and Closed Path Measurement of Atmospheric Trace Gases", *SPIE*, 2002, Aerodyne Research, Inc., 12 pages.

Jimenez, J. L., et al., "Cross Road and Mobile Tunable Infrared Laser Measurements of Nitrous Oxide Emissions from Motor Vehicles", *Chemosphere—Global Change Science*, vol. 2, 2000, pp. 397-412.

Rothman, L. S., et al., "The HITRAN Molecular Spectroscopic Database: Edition of 2000 Including Updates Through 2001", *Journal of Quantitative Spectroscopy &Radiative Transfer*, 2003, pp. 1-39.

McManus, J. B., et al., "Astigmatic Mirror Multipass Absorption Cells for Long-Path-Length Spectroscopy", *Applied Optics*, 1994, 14 pages.

Sonnenfroh, David M., et al., "Application of Balanced Detection to Absorption Measurements of Trace Gases with Room-Temperature, Quasi-cw Quantum-Cascade Lasers", *Applied Optics*, vol. 40, No. 6, Feb. 20, 2001, pp. 812-820.

Werle, P., et al., "The Limits of Signal Averaging in Atmospheric Trace-Gas Monitoring by Tunable Diode-Laser Absorption Spectroscopy (TDLAS)", *Applied Physics B*, vol. 57, 1993, pp. 131-139.

Kosterev, Anatoliy A., et al., "Trace-Gas Detection in Ambient Air with a Thermoelectrically Cooled, Pulsed Quantum-Cascade Distributed Feedback Laser", *Applied Optics*, vol. 39, No. 36, Dec. 20, 2000, pp. 6866-6872.

Faist, J., et at., "Sensitive Absorption Spectroscopy with a Room-Temperature Distributed-Feedback Quantum-Cascade Laser", *Optics Letters*, vol. 23, No. 3, Feb. 1, 1998, pp. 219-221.

Kelly, Kerry, et al., "Black Carbon and Polycyclic Aromatic Hydrocarbon Emissions from Vehicles in the United States-Mexico Border Region: Pilot Study", Technical Paper, *Journal of the Air &Water Management Association*, vol. 56, Mar. 2006, pp. 285-293.

Kurniawan, A., et al., "Monitoring the Soot Emissions of Passing Cars", *Environmental Science &Technology*, vol. 40, No. 6, 2006, pp. 1911-1915.

International Search Report and Written Opinion for PCT/US2012/040420 (filed Jun. 1, 2012) mailed Aug. 22, 2012, 9 pages.

\* cited by examiner ly to the quantification of the presence of one or more components in vehicle exhaust, and more particularly to a non-contact, extractive sampling system and method for quantifying the presence of one or more components in exhaust emissions of commercial and/or heavy-duty vehicles that emit exhaust at an elevated level, under actual operating conditions.

SYSTEM AND METHOD FOR QUANTIFYING THE PRESENCE OF COMPONENTS IN THE EXHAUST OF COMMERCIAL AND/OR HEAVY-DUTY VEHICLES

CROSS-REFERENCE TO RELATED APPLICATIONS

This Application is a continuation-in-part of U.S. patent application Ser. No. 13/052,815, filed Mar. 21, 2011 now U.S. Pat. No. 8,266,952, which is a continuation of U.S. patent application Ser. No. 12/114,189, filed May 2, 2008 (which issued as U.S. Pat. No. 7,930,931 on Apr. 26, 2011), each of which are hereby incorporated by reference herein in their entirety.

FIELD OF THE INVENTION

The invention relates generally to the quantification of the presence of one or more components in vehicle exhaust, and more particularly to a non-contact, extractive sampling system and method for quantifying the presence of one or more components in exhaust emissions of commercial and/or heavy-duty vehicles that emit exhaust at an elevated level, under actual operating conditions.

BACKGROUND OF THE INVENTION

Systems and methods for monitoring the exhaust gas composition and fine particle composition of exhaust emissions of various types of vehicles are known. For example, with regard to automobiles, it is common for emissions inspection stations (or automotive repair facilities) to utilize dynamometers for controlled engine loading tests for the purposes of exhaust emission measurement. One drawback associated with dynamometer testing, however, is that the measurements acquired often do not represent emissions under actual operating conditions when automobiles are in motion on a roadway or other driving surface.

To remedy these and other drawbacks associated with dynamometer testing, remote emissions sensing systems have been developed to remotely monitor the exhaust gas composition of automobiles traveling past "test sites" located along streets or highways. Examples of remote emissions sensing (or "cross-road") systems are described in, for example, U.S. Pat. Nos. 5,210,702, 5,319,199, 5,401,967, 5,591,975, 5,726,450, 5,797,682, 5,831,267, and 5,877,862, each of which is hereby incorporated herein by reference in its entirety.

However, existing systems configured to remotely test emissions tend to focus on passenger cars with exhaust systems that emit exhaust relatively close to the ground. By contrast, many commercial and/or heavy-duty vehicles, such as tractor-trailers, buses, commercial trucks, and/or other vehicles, have exhaust systems that emit exhaust at a point (or points) relatively high above the ground. For example, commercial diesel vehicles may include exhaust stacks that extend up vertically from the vehicles and emit exhaust up into the air.

As should be appreciated, exhaust leaving the exhaust pipe(s) of a moving commercial and/or heavy-duty vehicle (e.g., via exhaust "stacks" of a semi-tractor) is entrained in the vehicle's turbulent wake and continues to dissipate as the vehicle travels away. Despite the present turbulence, the dissipation of the exhaust will have a directionality associated with one or both of the location at which the exhaust is emitted and/or the direction in which it is propelled by momentum upon being emitted. For example, commercial and/or heavy-duty vehicles generally emit exhaust at an elevated position and/or propel emitted exhaust either upwards or to the side. As a result, remote emissions sensing systems designed to detect emissions for low-emitting vehicles (e.g., typical passenger automobiles) may not accurately quantify the presence of components in the exhaust of commercial and/or other heavy-duty vehicles.

Conventional remote sensing systems may further produce results that may not be indicative of the emissions of a commercial or heavy-duty vehicle because, depending on the placement of the remote sensing system and/or the operation of the commercial or heavy-duty vehicle, emissions from the vehicle may be measured while the vehicle is being operated in an atypical manner. For example, the emissions may be measured while the vehicle is changing gears. Measurements taken during a brief period of atypical operation may inaccurately indicate elevated levels of emission by the vehicle.

These and other problems can reduce the benefits of remote emissions sensing systems.

SUMMARY OF THE INVENTION

The invention addressing these and other drawbacks in the art relates generally to the quantification of the presence of one or more components in vehicle exhaust, and more particularly to a non-contact, extractive sampling system and method for quantifying the presence of one or more components in exhaust emissions of commercial and/or heavy-duty vehicles that emit exhaust at an elevated level (e.g., from a stack exhaust system), under actual operating conditions.

According to various implementations of the invention, to quantify the presence of one or more components in exhaust emissions of a commercial and/or heavy-duty vehicle that emits exhaust at an elevated level, a gathering structure and collector (or extraction tube) may be positioned directly over and/or adjacent to a path of the vehicle such that the gathering structure directs exhaust emitted by the vehicle at an elevated level above the roadway to the collector. The collector may receive at least a portion of the exhaust directed thereto by the gathering structure into one or more openings (or extraction holes) formed in the collector. A flow generator in fluid communication with the collector may generate a flow of air that draws exhaust directed to the collector by the gathering structure into the one or more openings of the collector. The flow of air generated by the flow generator may deliver the exhaust received into the one or more openings to a component detection system. Generally, the component detection system may quantify the presence in the exhaust of major gaseous exhaust species (e.g., concentrations of $CO_2$ or $H_2O$), along with the presence of one or more minor exhaust gases (e.g., carbon monoxide (CO), hycrocarbons (HC), oxides of nitrogen ($NO_x$), etc.), and/or fine particulate matter present in the exhaust (e.g., quantified as smoke, opacity, particle mass, particle scatter, etc.) so that emission indices for the minor exhaust gases and/or fine particulate matter that represent the amount of pollutants in the exhaust above background levels may be deduced.

In certain implementations, the gathering structure may be disposed at or near the roadway, and may have at least one surface that causes exhaust emitted by the vehicle at an elevated level (e.g., from a stack exhaust system) to gather around the collector. The roadway may be an actual road lane, and/or may be a separate test lane. In some implementations, the gathering structure may include a roof that spans the path of the vehicle in the roadway, and the collector may be disposed such that the collector openings are located at or near an underside surface of the roof. In such implementations, exhaust ejected by the vehicle may be gathered and pooled around the collector openings by the underside surface of the roof, which may facilitate the reception of the exhaust into the collector openings. In some instances, the gathering structure may be impermeable to one or both of .water and/or exhaust gases. In these instances, the gathering structure may further provide shelter for the collector openings and/or emitted exhaust from precipitation. Since the introduction of precipitation into the collector openings may interfere with the operation of the collector, the component detection system, and/or the flow generator generating the flow of air from the collector openings to the component detection system, the provision of shelter by the gathering structure may further enhance the collection and analysis of exhaust emitted by the vehicle at an elevated level.

According to various implementations, the gathering structure may include a tent-like structure. The roof of the gathering structure may be formed to guide exhaust that is emitted in a generally vertical direction toward the collector. For example, the roof of the gathering structure may be an "A-frame" root with the collector running along the underside of the roof at the interface between the two slopes of the "A-frame." The collector may be formed from a perforated pipe that runs along the underside of the roof at a position to which exhaust emitted in a substantially vertical direction is guided by the gathering structure.

In some implementations, the collector having one or more collector openings may be disposed along the path of the vehicle such that exhaust emitted by the vehicle at an elevated level (e.g., from a stack exhaust system) may be received into the one or more collector openings. The collector may include a conduit that communicates the received exhaust from the one or more collector openings to the component detection system that quantifies the presence of one or more components in the received exhaust.

In some implementations, the collector includes a plurality of collector openings that are arranged above the surface of a roadway along which the vehicle is traveling so as to receive the emissions of the vehicle, which are emitted at an elevated level (e.g., from high-stacks). For example, the collector may include a perforated pipe that forms the openings. In certain implementations, the collector may be disposed such that the collector openings are arranged along a path from between a first location and a second location that corresponds to the path of the vehicle between the first location and the second location. For example, the collector openings may be disposed in an array above the path of the vehicle between the first location and the second location to receive exhaust emitted upwards by the vehicle. This may facilitate the collection of exhaust by the collector openings, as exhaust emitted from the vehicle will be directed by momentum, turbulence, and/or other phenomena to the collector openings as the vehicle travels along the roadway.

According to some implementations, the flow generator may be configured to generate a flow of air that enables a continuous or periodic sampling of the air received into the collector openings at a predetermined flow rate. As the vehicle passes by the collector openings and exhaust from the vehicle is drawn into the collector openings toward the component detection system, the pressure in the conduit formed by the collector may decrease from atmospheric pressure at or near the collector openings, to a predetermined pressure level at a measurement space or cell associated with the component detection system where the presence of one or more components within the exhaust are quantified.

Characteristics of the collector and/or the collector openings (e.g., arrangement of the openings, length, diameter, cross-section, etc.), and/or operating parameters of the flow generator may be adjusted as necessary to achieve desired flow rates and pressure drops within the collector. Such adjustments to these and other components of the system may ensure that optimal conditions exist for quantifying the presence of one or more components in an exhaust sample delivered to the component detection system. Optimal conditions may vary depending on, for example, which molecular species of interest are being measured, as well as which type of component detection system is being implemented.

In various implementations, the collector may be configured such that collection times for exhaust emissions emitted by the vehicle to be conveyed through the collector to the component detection system vary as a function of position along the roadway. Collection times may be longer for locations that are closer to the first location, and shorter for locations that are closer to the second location. Since exhaust emissions are emitted first at the first location and then on toward the section location (e.g., as the vehicle proceeds along the roadway), the differences in collection times may cause exhaust emissions collected along the roadway to be aggregated into a condensed body of exhaust that is conveyed by the collector to the component detection system. To provide collection times that will result in exhaust emission aggregation, the size and/or shape of collector openings, the size and/or shape of lumen cross-section, lumen length, flow generator parameters, and/or other factors may be adjusted or configured. One or more of these factors may be controlled dynamically (e.g., based on vehicle speed) to ensure aggregation of the exhaust emissions. Aggregation of the exhaust emissions may increase the concentrations of the exhaust emissions, which may enhance the precision and/or accuracy of the analysis performed by the component detection systems.

According to an implementation of the invention, the component detection system may comprise any system capable of quantifying the presence of one or more components in exhaust. For instance, the component detection system may include a trace gas detection system comprising one or more of a mass spectrometer, visible/ultraviolet absorption spectrometer, infrared absorption spectrometer, and/or other component detection instruments or systems. In some instances, the component detection system may include a fine particle measurement system comprising one or more of an aerosol mass spectrometer, condensation particle counter, light scattering detector, laser incandescent particle detector, electrostatic particle charging detector, and/or other fine particle instruments or systems.

The system and method of the invention as disclosed herein may be utilized to quantify the presence of one or more components in a plurality of samples of exhaust taken according to a predetermined sampling rate. In some instances, the quantification of the one or more components in the exhaust for the plurality of samples may be aggregated in order to provide an aggregated quantification of the one or more components in the exhaust emitted by the vehicle. The aggregated quantification may provide an enhanced accuracy and/or precision in determining the quantity and/or nature of the emissions of the vehicle. For example, even if the vehicle is being operated in some atypical fashion (e.g., changing gears) along the pathway, the aggregation of the quantification may suppress inaccuracies caused by this momentary atypical operation. In some instances, the aggregated quantification may be determined by averaging the quantifications of the presence of the one or more components in the plurality of exhaust samples.

According to one or more implementations, for a given test period (e.g., a pass of the vehicle past the collector openings and/or the gathering structure), a computer (or processor) may correlate a record (or data file) of quantification of the one or more components in the exhaust of the vehicle with a record of an identity, or other information, associated with the vehicle (e.g., registration information, etc.).

Both the record and vehicle identification/information may be stored in a memory associated with, or accessible by, the computer. Data regarding the identification of those vehicles passing by the collector openings and/or the gathering structure may be acquired by an imaging unit or other known identification device or system in operative communication with the computer (e.g., via a wireless or hard-wired connection). Other vehicle identification systems may be implemented.

Various other objects, features, and advantages of the invention will be apparent through the detailed description of the invention and the drawings attached hereto. It is also to be understood that both the foregoing general description and the following detailed description are exemplary and not restrictive of the scope of the invention.

DETAILED DESCRIPTION OF THE INVENTION

Figure 1:
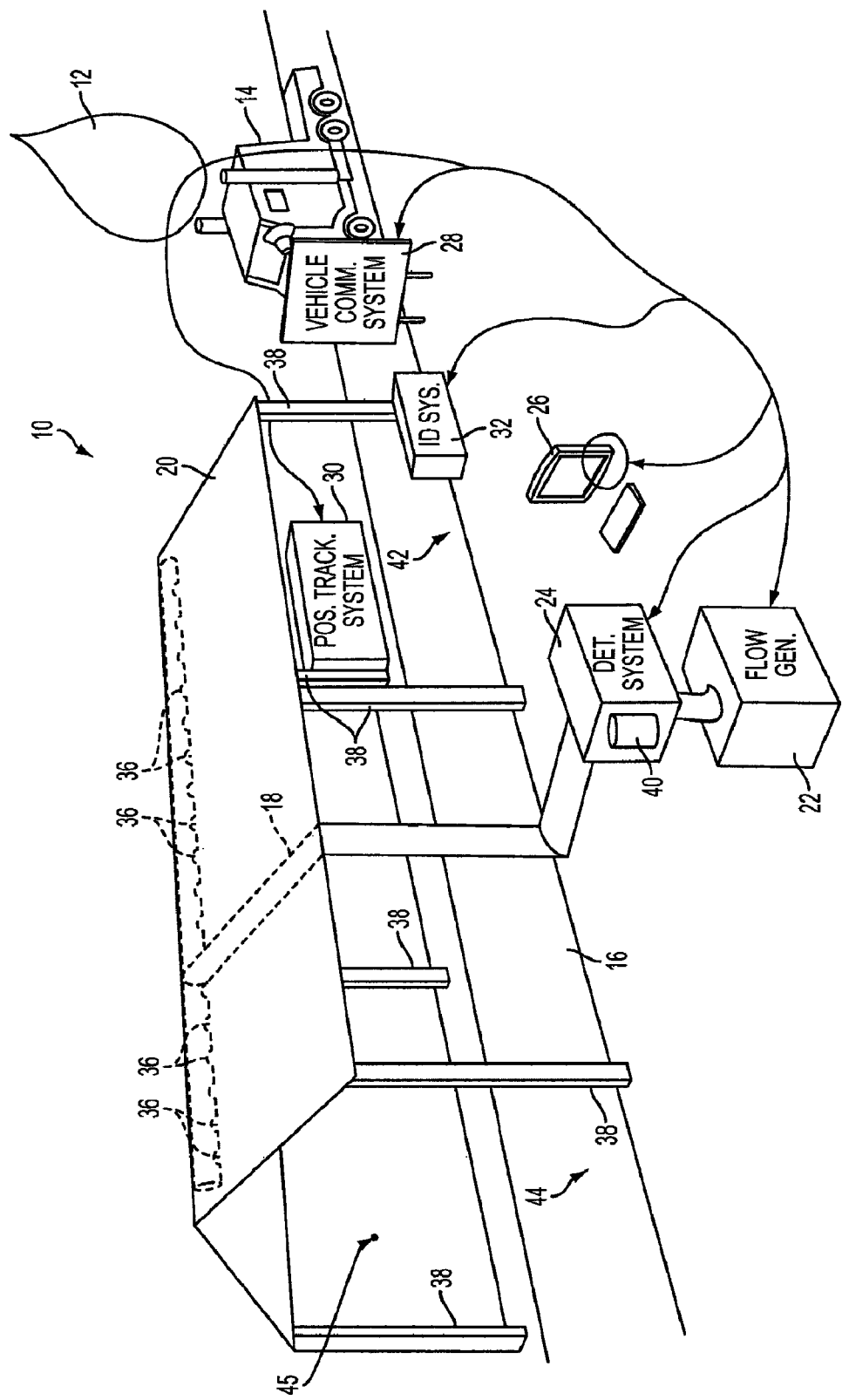
FIG. 1 illustrates a system for analyzing an exhaust plume of a vehicle traveling on a roadway, according to one or more implementations of the invention.

FIG. 1 illustrates a system 10 for analyzing an exhaust plume 12 of a vehicle 14 traveling on a roadway 16 under actual operating conditions, in accordance with one or more implementations of the invention. It should be appreciated that exhaust leaving the exhaust pipe(s) of moving vehicle 14 (e.g., via exhaust "stacks" of a semi-trailer or bus) is entrained in the vehicle's turbulent wake and continues to dissipate as vehicle 14 travels away. Despite the present turbulence, the dissipation of the exhaust will have a directionality associated with one or both of the location at which the exhaust is emitted and/or the direction in which it is propelled by momentum upon being emitted. For example, commercial and/or heavy-duty vehicles generally emit exhaust at an elevated position and/or propel emitted exhaust either upwards or to the side. As a result, remote emissions sensing systems designed to detect emissions for low-emitting vehicles (e.g., typical passenger automobiles) may not accurately quantify the presence of components in the exhaust of commercial and/or other heavy-duty vehicles.

Roadway 16 may comprise any driving surface suitable for safe passage of vehicle 14, and may further comprise a single vehicle travel lane, or multiple vehicle travel lanes. Roadway 16 may comprise a road along which vehicle 14 is traveling to its destination, or roadway 16 may comprise a separate test lane (or lanes) to which vehicle 14 has detoured from its route in order to have its emissions tested separate from other traffic. System 10 may be particularly suited to analyze exhaust where vehicle 14 is a semi-trailer truck, dump truck, tractor, bus, etc. that emits gas at an elevated level (in comparison with low emitting passenger vehicles), such as through a stack exhaust emission system.

In some implementations, system 10 may include one or more of a collector 18 (or extraction tube), a gathering structure 20, a flow generator 22, a component detection system 24, a computer 26, a vehicle communication system 28, a position tracking system 30, a vehicle identification system 32, and/or other components. As will be discussed further below, exhaust from exhaust plume 16 may be gathered by gathering structure 20 around collector 18, and pulled or extracted through collector 18, via suction generated by flow generator 22, to component detection system 24 where the presence of one or more components within the exhaust may be quantified. Upon analysis of the air provided to component detection system 24 through collector 18, the analyzed air may be exhausted from system 10 via an exit pipe.

According to various implementations, gathering structure 20 may have one or more surfaces that cause exhaust emitted by vehicle 14 to gather around one or more collector openings 36 (or extraction holes) formed in collector 18. Collector 18 may be disposed at or near such surfaces of gathering structure 20. This may facilitate the reception of exhaust into collector openings 36, as the exhaust gathered by gathering structure 20 remains concentrated around collector openings 36 for a relatively prolonged period of time, during which the gathered exhaust may be drawn into collector 18 via collector openings 36. In some instances, collector 18 may include a conduit, or conduits, formed integrally with gathering structure 20. In such instances, collector openings 36 may be formed as openings in a surface of gathering structure 20 that communicate with the conduit, or conduits, formed integrally with gathering structure 20.

In some implementations the one or more surfaces of gathering structure 20 that cause exhaust emitted by vehicle 14 to gather around one or more of collector openings 36 may be impermeable (or substantially so) for one or both of exhaust emitted by vehicle 14 and/or water. In such implementations, gathering structure 20 may protect collector openings 36 from precipitation. This may facilitate analysis of exhaust received by collector openings, as the introduction of ambient water from precipitation into exhaust may complicate one or both of transport of the exhaust by collector 18 and/or analysis of the collected exhaust.

In some instances, gathering structure 20 may include a roof. The roof may be positioned over some or all of roadway 16. The roof may provide the one or more of the surfaces that gather exhaust emitted by vehicle 14 around collector openings 36. The roof may be an "A-frame" roof, with collector 18 running along at or near the interface between the two planes that form the "A-frame" roof (or the "peak" of the roof). The roof may be supported a plurality of trusses (not shown). The trusses may run substantially perpendicular to the general direction of gathering structure 20. The roof may be supported above roadway 16 by one or more load-bearing supports 38. Supports 38 may include one or more vertical structures with spaces in between.

In some implementations, gathering structure 20 may further comprise one or more solid vertical planes (e.g., walls) that extend parallel to a direction of travel on roadway 16. The height of the walls may vary such that the walls may extend from the roof all the way down to the ground surface, or partially down to the ground surface. Additionally, the length of the walls may vary such that the walls may extend the entire length of gathering structure 20, or only along a portion of the length of gathering structure 20. The solid vertical planes (or walls) may be rigid, or may alternatively be formed of flexible, plastic material (e.g., such as flexible, plastic sheets (or aprons)). If the walls are rigid and load-bearing, then supports 38 may not be necessary. By contrast, if the walls are formed of flexible, plastic sheets (or aprons), the one or more load-bearing supports 38 (or other types of supports for the roof of gathering structure 20) may be provided.

In some implementations, either or both of the flexible, plastic sheets (or aprons) comprising the walls of gathering structure 20 may be transparent so as to not adversely impact the visibility of the driver of vehicle 14. For example, if roadway 16 comprises a separate test lane (or lanes) to which vehicle 14 has detoured from its route in order to have its emissions tested separate from other traffic, the use of transparent plastic sheets (or aprons) may be beneficial in that the driver of vehicle 14 will be able to better see/monitor traffic conditions when, for example, departing gathering structure 20 and merging back into traffic.

In various implementations, walls (as described above) may be provided on either or both sides of gathering structure (20). In some instances, no walls may be provided and the roof of gathering structure may, as described above, be supported above roadway 16 by one or more load-bearing supports 38 comprising vertical structures (e.g., posts, columns, etc.) with spaces in between. Configuring gathering structure 20 to include one, two, or no walls extending parallel to a direction of travel on roadway 16 may depend on a variety of factors including, for example, the types of vehicles being tested. For example, if commercial and/or heavy-duty vehicles are being tested that have exhaust "stacks" that emit exhaust in an upward (vertical) direction, it may not be necessary to include walls as the roof of gathering structure 20 may direct exhaust emissions to (or pool exhaust emissions near) one or more openings 36 of collector 18. Some "high-stack" vehicles, however, have exhaust stacks that direct emissions outward (laterally) away from the vehicle at an elevated position. One example includes smaller rock hauler trucks that have exhaust stacks that are positioned lower and that aim sideways to the right. Having a wall on the same side of gathering structure 20 as the side of vehicle 14 where exhaust gases are emitted would help contain vehicle exhaust emissions within gathering structure 20 and/or guide such emissions toward one or more openings 36 of collector 18.

The configuration of roadway 16 may also factor into a determination as to whether walls may be provided on either or both sides of gathering structure 20. For example, if roadway 16 comprises a separate test lane (or lanes) to which vehicle 14 has detoured from its route in order to have its emissions tested separate from other traffic, gathering structure 20 may not include a wall on its left side, particularly if vehicle 14 emits exhaust to the right-hand side and has to merge back into traffic on its left-hand side (so as to improve visibility for the driver). Alternatively, gathering structure 20 may not include a wall on its right side, particularly if vehicle 14 emits exhaust to the left-hand side and has to merge back into traffic on its right-hand side (so as to improve visibility for the driver). In the exemplary and non-limiting illustration of FIGS. 1-2, gathering structure 20 is depicted with only one side wall 45 (on the right-hand side) extending parallel to a direction of travel on roadway 16.

If a variety of high-stack emitters will likely be encountered during a testing session, including those that emit exhaust emissions either vertically, to the left-hand side, and/or to the right-hand side such that it is desirable to have walls on both sides of gathering structure 20, then, as noted above, gathering structure 20 may comprise two walls comprising flexible, plastic sheets (or aprons) that are transparent so as to not adversely impact the visibility of the driver of vehicle 14. Alternatively, if roadway 16 comprises a separate test lane (or lanes) of sufficient length such that vehicle 14 has an ample distance to merge back into traffic after departing gathering structure 20, either or both of the walls of gathering structure 20 may be rigid, or plastic (but not necessarily transparent). Many different configurations may be implemented.

In some implementations of the invention, collector 18 receives air from one or more collector locations above the surface of roadway 16. Collector 18 may be held in place at or near gathering structure 20 by one or more of a variety of different techniques for securing collector 18 in place. These techniques may include, for example, fastening collector 18 to gathering structure 20 with an adhesive and/or one or fasteners (e.g., one or more U-bolts), and/or other techniques. Collector 18 may include one or more conduits with one or more collector openings 36 formed therein. For example, collector 18 may be formed from one or more perforated pipes. Air can be drawn into collector 18 from ambient atmosphere via collector openings 36. Each of the collector openings 36 may form one of the aforementioned collector locations.

The position of collector openings 36 with respect to roadway 16 may facilitate reception by collector openings 36 of exhaust from vehicle 14 where vehicle 14 is a commercial or heavy-duty vehicle. For example, collector 18 is illustrated in FIG. 1 and discussed herein as providing collector openings 36 over roadway 16 to receive exhaust emitted at an elevated location and/or with an upward velocity by vehicle 14 (e.g., from the "stacks" on a semi-tractor, etc.). This is not intended to be limiting. For example, in some implementations, collector 18 may provide collector openings along side roadway 16 above the surface of roadway 16 (e.g., to collect exhaust emitted by vehicles that project exhaust out to the side). In certain implementations, collector 18 may include a single conduit along which collector openings 36 are formed (as shown in FIG. 1). In certain implementations, collector 18 may include a plurality of separate conduits and/or conduit branches, with each of the conduits and/or conduit branches forming one or more of collector openings 36.

In some implementations of the invention, collector openings 36 may be disposed between a first location and a second location on the roadway. The path between the first location and the second location may correspond to the path of vehicle 14 as it travels along roadway 16 (e.g., the path defined for vehicle 14 by roadway 16). For example, as may be seen in FIG. 1, in some implementations, collector openings 36 may be disposed above the path of vehicle 14 along the roadway to receive exhaust emitted by vehicle 14.

In some implementations of the invention, one or both of collector 18 and/or gathering structure 20 may be portable between sites. For example, collector 18 may be removable from gathering structure 20 to enable collector 18 to be selectively implemented at a plurality of different sites that have gathering structures. As another example, gathering structure 20 may include a tent-like structure, or some other portable structure that enables gathering structure 20 to be transported with collector 18 between sites.

Flow generator 22 may be in communication with collector 18, and may be configured to generate a flow of air within collector 18 that draws ambient air present at the collector locations into collector openings 36, and through the conduit(s) formed by collector 18. As such, flow generator 22 may generate a negative pressure at an end of the conduit(s) of collector 18 opposite collector openings 36 to create suction that draws the ambient air into collector openings 36. Flow generator 22 may include a vacuum pump, an impeller (or turbine), and/or other flow generators capable of generating a flow of air from collector openings 36 down into the conduit(s) of collector 18.

In some implementations, flow generator 22 may be configured to continuously draw air into collector 18 at a predetermined flow rate (e.g., 5.0 standard liters per minute) from collector openings 36. As vehicle 14 passes by collector 18, a plug (or plugs) of air including a sample of exhaust plume 16 may be drawn through collector openings 36 and into the conduit(s) formed by collector 18. The air received thusly may be delivered from collector 18 to component detection system 24 (with which the conduit(s) of collector 18 is in fluid communication) for analysis, as is discussed below. The plug(s) of air including the exhaust sample remains essentially intact with minimal spreading as it travels through collector 18. The length of the conduit(s) between collector openings 36 and component detection system 24 may differ in various configurations as the distance between roadway 16 and component detection system 24, the height of collector openings 36 from the surface of roadway 16, and/or other system parameters vary.

At collector openings 36, air may be substantially at atmospheric pressure. As was mentioned above, to induce a flow of air within collector 18 that draws air into collector openings 36, flow generator 22 may generate a reduced pressure within collector 18 that falls to a predetermined pressure level at or near a measurement cell 40 associated with component detection system 24, at which the presence of one or more components in the air received from collector openings 36 may be quantified. In some instances, for example, the pressure in measurement cell 40 may decrease to approximately 50 torr. In one implementation, and as illustrated in FIG. 1, for example, flow generator 22 may be located downstream of the measurement instruments comprising component detection system 24. In such a configuration, detectors (of component detection system 24) may be sampling under slight vacuum conditions. Alternatively, flow generator 22 may be located upstream of the measurement instruments comprising component detection system 24 (not illustrated). In this instance, detectors (of component detection system 24) may be sampling under atmospheric pressure, however, the blades of the turbine of flow generator 22 may disrupt some particles.

In various implementations, and as described in greater detail below with reference to FIG. 2, characteristics of collector 18 (e.g., arrangement of openings, length, diameter, cross-section, etc.), and/or operating parameters of flow generator 22 may be adjusted as necessary to achieve desired flow rates and pressure drops within collector 18. Such adjustments to these and other components of system 10 may ensure that optimal conditions exist for quantifying the presence of one or more components in exhaust plume 14. Optimal conditions may vary depending on which components are being analyzed (e.g., which gaseous components, what size particulate matter, etc.), as well as what type of component detection system 24 is being implemented to best quantify the presence of the components of interest.

According to an implementation of the invention, component detection system 24 may comprise any system capable of quantifying the presence of one or more components in a sample of exhaust introduced into a measurement space or cell 40 (via collector 18 and flow generator 22). As such, component detection system 24 may comprise a detector capable of determining concentrations of one or more gaseous constituents present in an exhaust sample, a detector capable of measuring the density of particulate matter present in an exhaust sample (e.g., opacity, smoke, etc.), and/or other detectors. For example, component detection system 24 may comprise a mass spectrometer, visible/ultraviolet absorption spectrometer, infrared absorption spectrometer, or other known or subsequently developed trace gas detection instrument or system. Similarly, component detection system 24 may comprise an aerosol mass spectrometer, condensation particle counter, light scattering detector, laser incandescent particle detector, electrostatic particle charging detector, or other known or subsequently developed fast response, fine particle instrument or system.

Similar to most (if not all) non-contact, remote emissions sensing (or "cross-road") systems, including (but not limited to) those systems described in the U.S. Patents identified (and incorporated herein by reference) above, component detection system 24 may, in one implementation, be configured to determine the ratio of individual pollutants (e.g., CO, HC, NO, etc.) to $CO_2$ or to total carbon in a known manner to determine the concentration of the individual pollutants in an exhaust gas sample. The individual concentrations of pollutants in diluted exhaust may not in themselves be useful until assembled into ratios versus $CO_2$ from which can be determined emissions per kg of fuel, per gallon of fuel and, to a good approximation, to emissions per brake horsepower hour (the units of the current government standard for new engine certification) to the extent that fuel consumption per brake horsepower hour is reasonably well known for heavy duty diesel engines. Because ratios are used, it may not matter, for example, if one of the extractive measurement instruments (of component detection system 24) is slower in response than the others, or has a greater lag time before reporting concentrations versus time. This may arise because, for each instrument, there may be a few seconds when an exhaust plume is known to be present (e.g., from the $CO_2$ data with some extra time added on each side) and the pollutant readings in the other instruments will be integrated during that time frame, and then the integrals ratioed to the observed $CO_2$ integral. In an illustrative (and non-limiting) example, a $CO_2$ detector may have a slower response time than a CO detector, and vehicle exhaust being measured may include both CO and $CO_2$ (above "background" levels). Further, in the example, a two-second, long plume of well-mixed exhaust arrives at the detector manifold (of component detection system 24). The CO detector (having a faster response time) correctly measures a two-second long peak which is measured and integrated above the background reading, while the slower $CO_2$ detector may measure a four-second peak before it returns to the background reading. However, each peak may be integrated regardless of the exact time when the measurement was recorded, and the ratio of the two integrals may be used as the average exhaust $CO/CO_2$ ratio from which emissions per kg of fuel, per gallon of fuel, etc. are calculated.

In one implementation, background exhaust gas concentrations may, as in other remote sensing applications, be determined from the instrument readings (of component detection system 24) before and/or after an observed $CO_2$ plume from vehicle 14 passing through gathering structure 20 is recorded.

Further, calibration of component detection system 24 may be provided by inserting a puff of suitable synthetic exhaust gas with known RATIOs into one or more of collector openings 36 or a separate calibration gas entrance (not illustrated) upstream of component detection system 24 to guarantee adequate mixing. Calibration of smoke parameters may be achieved using known calibration procedures (e.g., the extractive instrument manufacturer's calibration procedures).

According to one aspect of the invention, computer 26 may be in operative communication with and/or control one or more components of component detection system 24, flow generator 26, vehicle communication system 28, position tracking system 30, vehicle identification system 32, and/or other components. For example, computer 26 may control a data acquisition (or sampling) session, as well as process and store data from component detection system 24. Computer 26 may comprise a personal computer, portable computer (e.g., laptop computer), processor, or other device. In some implementations, computer 26 may comprise one or more of one or more processors, a user interface, memory, one or more storage devices, and/or other components, which are electrically coupled via a bus. The memory may comprise random access memory (RAM), read only memory (ROM), or other memory. The memory may store computer-executable instructions to be executed by the one or more processors, as well as data which may be manipulated by the one or more processors. The one or more storage devices may comprise floppy disks, hard disks, optical disks, tapes, or other storage devices for storing computer-executable instructions and/or data. The user interface may comprise interfaces to various peripheral devices (e.g., keyboard, mouse, microphones, external storage devices, monitors, printers or other input and/or output devices as would be appreciated by those having skill in the art) as well as other components as described herein.

According to one aspect of the invention, computer 26 may be connected by wire or wirelessly to a network (e.g., Internet, Intranet, etc.) so that emissions data or other information may be made accessible via a web site or other application (or transmitted a predetermined interval) to vehicle owners or operators, regulatory bodies (e.g., Dept. of Motor Vehicles), or to other entities.

In some implementations, component detection system 24 takes a plurality of "samples" of exhaust emitted by vehicle 14 as vehicle 14 is adjacent to (or, e.g., driving through or under) gathering structure 20. This may comprise quantifying the presence of one or more components (e.g., gaseous constituents, particulate matter, etc.) in air collected by collector 18 periodically at a sampling rate over a time period during which exhaust emitted by vehicle 14 while operating adjacent to gathering structure 20 is being analyzed. For example, this time period may include a time period during which exhaust emitted by vehicle 14 while traveling from a first location 42 at or near a first end of (or entrance to) gathering structure 20 to a second location 44 at or near an opposite (or second) end of (or exit from) gathering structure 20 is being analyzed by component detection system 24. In some instances, component detection system 24 (or some subsequent processor, such as computer 26) aggregates the samples taken during the time period to determine an aggregate quantification of the presence of the one or more components in the exhaust of vehicle 14. Even if the vehicle is being operated in some atypical fashion (e.g., changing gears) during the time period, the aggregation of the quantification may suppress inaccuracies caused by this momentary atypical operation, and may be more representative of the emissions of vehicle 14 under normal driving conditions that a conventional remote sensing measurement. For example, values determined for each of the samples may be averaged or otherwise aggregated to determine the aggregate quantification of the presence of the one or more components in the exhaust of vehicle 14.

In some instances, readings of component detection system 24 may be implemented as a "trigger" that causes an aggregation of measurements of exhaust components present in the air within collector 18. For example, a rise in $CO_2$, and/or some other exhaust component, in the air within collector 18 (as determined by component detection system 24) above some predetermined threshold may trigger the an aggregation of samples taken by component detection system 24. The aggregation may continue until the $CO_2$ within the air in collector 18 falls below the predetermined threshold, for a predetermined time period after the initial trigger, for a predetermined time period after the level of $CO_2$ falls below the threshold, and/or for some other amount of time.

As should be apparent from the configuration of collector 18 and gathering structure 20 with respect to roadway 16, system 10 is configured to detect the presence of components in the exhaust of vehicle 14 during normal operation of vehicle 14. Generally, the amount and composition of exhaust emitted by a vehicle is somewhat a function of the conditions under which the vehicle is operating. For example, exhaust emitted by vehicle 14 while cruising at freeway speeds on a level grade would be expected to be different in quantity and/or composition from exhaust emitted by vehicle 14 while accelerating from a stopped position.

As such, vehicle communication system 28 may be provided to communicate with the driver of vehicle 14 the manner in which vehicle 14 should be operated while it is traveling along the path of roadway 16 that is adjacent to collector openings 36 (e.g., underneath collector openings 36 between first location 42 and second location 44). For example, vehicle communication system 28 may communicate instructions to the driver of vehicle 14 dictating the manner in which vehicle 14 should be operated. In one implementation, the instructions may include: (1) an instruction to bring vehicle 14 to a stop, or some predetermined low speed, at first location 42 at one end of gathering structure 20; and (2) an instruction to accelerate from the stop (or low speed) while traveling along the roadway adjacent to gathering structure 20 toward second location 44. The instruction to accelerate may include a predetermined upper speed that vehicle 14 should reach before exiting the section of roadway adjacent to gathering structure 20 (e.g., at second location 44), a rate of acceleration, and/or other instructions that specify how much vehicle 14 should accelerate. In one implementation, the instructions may include a speed at which vehicle 14 should be driven for the entire time that it is on roadway 16 between first location 42 and second location 44. Other implementations, in which vehicle communication system 28 communicates other operating conditions to the driver of vehicle 14 exist.

In order to communicate with the driver of vehicle 14, vehicle communication system 28 may include one or more displays, one or more speakers, and/or other interfaces that communicate information to the driver of vehicle 14. In some implementations, the one or more displays may include one or more dynamic, electronic displays (e.g., monitors, screens, projectors, lights, etc.) that can be controlled to provide information to the driver of vehicle 14. In some implementations, the one or more displays may include one or more static, fixed displays (e.g., signs, lettering/figures formed on roadway 16, lettering/figures formed on gathering structure 20, etc.), and/or other displays.

Although vehicle communication system 28 may be positioned proximate to gathering structure 20 and/or collector

18, in some implementations, vehicle communication system 28 may provide communication to the driver of vehicle 14 at some predetermined distance from gathering structure 20 and/or collector 18. For example, at some predetermined distance from gathering structure 20 and/or collector 18, vehicle communication system 28 may communicate to the driver of vehicle 14 that a test zone at which the emissions of vehicle 14 will be tested is upcoming, and that vehicle 14 should achieve and/or maintain some predetermined speed while adjacent to gathering structure and/or collector 18.

In some implementations of the invention, position tracking system 30 may track the position, speed, acceleration, jerk, etc. of vehicle 14 as it travels along roadway 16 between first location 42 and second location 44. Position tracking system 30 may include one or more of infrared motion sensors, pressure sensors, radar, lidar, sonar, and/or or other sensors capable of detecting the presence, speed, acceleration, etc. of vehicle 14.

The information determined by position tracking system 30 may be communicated to computer 26, and may be processed by computer 26 to determine the compliance of vehicle 14 with the instructions provided by vehicle communication system 28. This may enable computer 26 to "flag" instances where vehicle 14 has not been operated in accordance with the operating conditions dictated by vehicle communication system 28 (e.g., as invalid, as being of questionable accuracy and/or precision, etc.).

In some instances, the information determined by position tracking system 30 may be implemented to determine when exhaust emitted by vehicle 14 is being analyzed by component detection system 24 (as opposed to ambient air). For example, as was mentioned above, there is generally a delay between the reception of exhaust at collector openings 36 and introduction of the received exhaust into component detection system 24 (e.g., within measurement cell 40). The detection of the position of vehicle 14 along roadway 16, coupled with a known amount of time associated with this delay may enable a determination (e.g., by computer 26) as to when the exhaust emitted by vehicle 14 and received at collector openings has reached component detection system 24.

In some implementations, information related to the position of vehicle 14 by position tracking system 30 may be implemented to "trigger" operation of one or both of flow generator 22 and/or component detection system 24. For example, a determination by position tracking system 30 that vehicle 14 is at or approaching gathering structure 20 (e.g., at or approaching first location 42) may trigger flow generator 22 to begin to generate a flow of air from collector openings 36 to component detection system 24. In such instances, flow generator 22 may begin to generate a flow by opening a valve (e.g., to communicate the conduit(s) associated with collector 18 with a reduced pressure chamber), initiating a pump (e.g., to begin suction), and/or otherwise generating a flow from collector openings 36 to component detection system 24. Similarly, flow generator may cease the generation of a flow from collector openings 36 to component detection system upon a determination by position tracking system 30 that vehicle 14 is exiting, or has exited, gathering structure 20.

Data regarding the identification of those vehicle 14 passing adjacent to gathering structure 20 to have its exhaust tested may be acquired by vehicle identification system 32 or other known identification device or system (not illustrated) in operative communication with computer 26 (e.g., via a wireless or hard-wired connection). Vehicle identification system 32 may comprise, for example, a film camera, video camera, or digital camera. Other imaging devices may also be used. Preferably, the imaging unit associated with vehicle identification system 32 may record an image of the identification tag (e.g., license plate) of vehicle 14. Tag information may be processed by computer 26 to provide additional information about vehicle 24. For example, a Motor Vehicle Department databases may be accessed to retrieve owner information, driver information, license information, make, model type, model year, or other information.

According to one implementation of the invention, an identification tag on vehicle 14 may be read by vehicle identification system 32 to identify the vehicle, and computer 26 may associate particular sensed vehicle emission information with the identified vehicle. In some implementations, an identification tag (defined as a license plate above), may comprise a transponder located on or within vehicle 14 (e.g., hung from a rear view mirror, placed on the dashboard, etc.), or that is integral within the vehicle (e.g., part of a global positioning system ("GPS"), located within the engine of the vehicle, or placed or mounted elsewhere). The transponder may transmit information about vehicle 14, including make and model of vehicle 14, engine characteristics, fuel type, the owner of vehicle 14, or other information which may be pertinent. Information transmitted by the transponder may be received by vehicle identification system 32. According to an implementation of the invention, a transponder may be used in connection with other functions. By way of example, a transponder may also be used in connection with a toll pass, whereby a driver can electronically pay tolls via the transponder without stopping the vehicle.

An identification tag may also comprise a tag or decal that requires a reader associated with vehicle identification system 32. By way of example, an identification tag may comprise a decal with identifying marks (e.g., bar codes, infrared markings, etc.) containing information about vehicle 14. The decal may be located outside vehicle 14, such as on a front or rear bumper, on the under-side of vehicle 14, or any other location on vehicle 14 where the decal may be suitably read. A reader may observe the decal and thereby obtain information about vehicle 14.

Computer 26 may receive information about vehicle 14 from a reader and/or receiver associated with vehicle identification system. Vehicle information and information obtained by sensing vehicle emissions may be stored. Computer 26 may correlate vehicle information received from an identification tag with the results from vehicle emissions sensing. Computer 26 may update a vehicle record to include results obtained by processing vehicle emission data, such as information regarding whether a vehicle has passed or failed predetermined emissions criteria. Other vehicle identification systems may be implemented.

Figure 2:
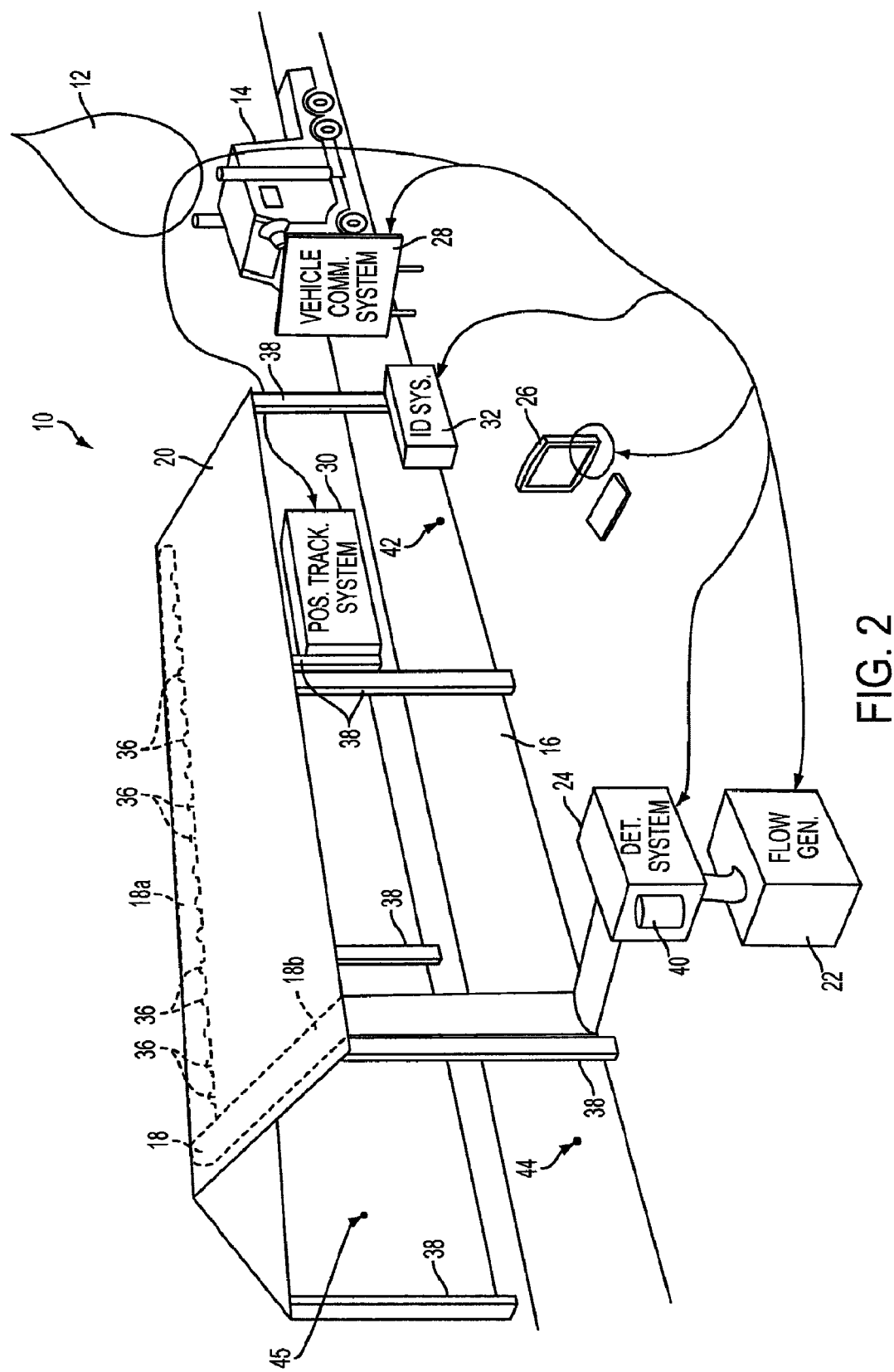
FIG. 2 illustrates a system for analyzing an exhaust plume of a vehicle traveling on a roadway, according to one or more implementations of the invention.

FIG. 2 illustrates an exemplary (non-limiting) implementation of system 10. As shown, collector 18 may include an extraction portion 18a, a delivery portion 18b, and/or other portions. Extraction portion 18a may include the portion of collector 18 in which collector openings 36 are formed, and may be configured to extract vehicle emissions that have been gathered (or directed) into openings 36 by gathering structure 20. Delivery portion 18b may be configured to deliver vehicle emissions (that have been extracted by extraction portion 18a) to component detection system 24.

The emission extraction subsystem formed by extraction portion 18a, delivery portion 18b, collector openings 36, and flow generator 22 may be configured such that the time it takes vehicle emissions extracted at a given one of collector openings 36 to reach delivery portion 18b and/or component detection system 24 is a function of the location of the given collector opening 36 between first location 42 and second location 44. In some implementations, vehicle emissions extracted through one or more collector openings 36 closer to first location 42 take longer to reach delivery portion 18b than vehicle emissions extracted through one or more collector openings 36 closer to second location 44. For convenience, the time it takes for a sample of vehicle exhaust emissions to travel from an entry point in extraction portion 18a (e.g., entry being via one or more collector openings 36) to component detection system 24 will be referred to herein as the "collection time" of the sample.

As vehicle 14 is traveling on roadway 16 (as shown in FIGS. 1-2) in a direction from first location 42 toward second location 44, exhaust emissions from vehicle 14 arrive at one or more collector openings 36 near first location 42 before exhaust emissions from vehicle 14 arrive at one or more collector openings 36 near second location 44. As such, by configuring one or more of extraction portion 18a, delivery portion 18b, collector openings 36, and/or flow generator 22 such that the collection time of a (first) sample of vehicle emissions extracted at one or more collector openings 36 located near first location 42 is longer than the collection time of a (second) sample of vehicle emissions extracted at one or more collector openings 36 located near second location 44, exhaust emissions emitted by vehicle 14 between first location 42 and second location 44 (along roadway 16) are aggregated and/or condensed for analysis by component detection system 24.

In other words, a sample of exhaust emissions emitted by vehicle 14 relatively close to first location 42 may be introduced into delivery portion 18b of collector 18 at substantially the same time as a sample of exhaust emissions emitted later in time when vehicle 14 is relatively close to second location 44. This aggregation of vehicle emissions results in an integrated (or aggregated) exhaust plume (or sample) that is larger and easier to measure, thereby enhancing the accuracy and/or precision of the analysis performed by component detection system 24 (e.g., the determination of the concentrations of the gaseous components in the integrated sample).

In one implementation, a delay in collection time along extraction portion 18a of collector 18 may be manipulated and/or controlled to substantially match the travel time of vehicle 14 along roadway 16. For example, if instructions provided to an operator of vehicle 14 (e.g., by vehicle communication system 28) result in a trip between first location 42 and second location 44 having some trip duration, one or more of extraction portion 18a, delivery portion 18b, collector openings 36, and/or flow generator 22 may be configured such that a collection time for a (first) sample of vehicle exhaust emissions collected through one or more collector openings 36 at or near first location 42 is longer than a collection time for a (second) sample of vehicle exhaust emissions collected through one or more collector openings 36 at or near second location 44, with the difference in collection times for the first and second samples being substantially equal to the trip duration. This difference in collection times may be determined, for example, based on a predicted trip duration (e.g., the trip duration if directions conveyed via vehicle communication system 28 are followed). Such directions may include instructions to maintain a given speed, accelerate, and/or deccelerate. The difference in collection times may also be determined based on measurements of vehicle position and/or speed (e.g., by position tracking system 30), and/or determined in other ways.

A difference in collection times may be created in one or more of a variety of ways. For example, by positioning the interface between extraction portion 18a and delivery portion 18b relatively close to second location 44 (e.g., at or near second location 44), a sample of vehicle exhaust emissions entering extraction portion 18a at or near first location 42 will have to travel the full length of extraction portion 18a to reach delivery portion 18b, while a sample of vehicle exhaust emissions collected at or near second location 44 will have a much shorter path within extraction portion 18a before reaching delivery portion 18b.

As another example, the size and/or shape of collector openings 36 may be varied over the length of extraction portion 18a to increase or decrease the rates at which exhaust emissions are collected into extraction portion 18a through individual collector openings 36. In one implementation, for example, the size (diameter) and/or shape of collector openings 36 at or near first location 42 may be larger than the size (diameter) and/or shape of collector openings 36 at or near second location 42.

In one non-limiting example, the size and/or shape of one or more of collector openings 36 may be static or dynamic (e.g., formed by controllable valves having variable opening size and/or shape).

As yet another non-limiting example, the rate at which flow generator 22 pulls exhaust gases through delivery portion 18b may be adjusted to adjust the differences in collection times for vehicle emissions collected closer to first location 42 and vehicle emissions collected closer to second location 44. Other mechanisms for controlling the collection times may be used in conjunction with or separate from those set forth herein.

The illustration of collector 18 as including a single path as extraction portion 18a and a single path as delivery portion 18b should not be viewed as limiting. In some implementations, collector 18 may include a plurality of separate lumens or other structures operating as extraction portions 18a and/or a plurality of separate lumens or other structures operating as delivery portions 18b. In some implementations, the inclusion of a plurality of separate extraction portions 18a and/or delivery portions 18b may enhance the ability to dynamically adjust collection times for vehicle exhaust emissions gathered and/or collected (via collector 18) at different locations between first location 42 and second location 44. This may facilitate active adjustment of collection times to accommodate different trip durations for vehicle 14 along roadway 16.

In view of the foregoing description, one exemplary and non-limiting example is provided with reference to FIG. 2. Particularly, in the example, extraction portion 18a of collector 18 may be approximately fifty feet in length, and collector openings 36 near first location 42 may be larger than the collector openings 36 near second location 44 (near delivery portion 18b). If vehicle 14 enters gathering structure at or near first location 42 and takes approximately eight seconds to travel through gathering structure 20 before arriving at second location 44, then a second sample of vehicle emissions extracted at a collector opening 36 located near second location 44 will be entering the collector opening 36 at approximately the same time as a first sample of vehicle emissions previously extracted near first location 42 arrives inside extraction portion 18a (just inside the same collector opening 36 near second location 44). This configuration assumes that flow generator 22 is configured to draw the first sample of vehicle emissions (extracted near first location 42) through the fifty-foot extraction portion 18a in approximately eight seconds. As a result, when eight seconds worth of exhaust samples from vehicle 14 arrive at second location 44 (near delivery portion 18b), they are integrated into a sample of dilute exhaust (i.e., the second sample of vehicle emissions extracted at a collector opening 36 located near second location 44) with a much shorter time profile than the eight seconds spent contributing to the air flow. This integration (in which eight seconds of exhaust samples is placed into about two seconds worth of air) compliments the integration to be performed by the suite of instruments comprising component detection system 24.

The location of delivery portion 18b may be altered to change the dilution of exhaust from vehicle 14 so as to achieve readings most suitable for the suite of instruments comprising component detection system 24, and to ensure adequate exhaust dilution to avoid water condensation, inappropriate particle formation, or other occurrences that may negatively affect testing accuracy. Maximum dilution may, for example, be achieved when delivery portion 18b is located substantially near the entrance of gathering structure 20 near first location 42. By contrast, minimum dilution may, for example, be achieved when delivery portion 18b is located substantially near the exit of gathering structure 20 near second location 44 (as shown in FIG. 2). In various implementations, delivery portion 18b may be located at any point along gathering structure 20 between first location 42 and second location 44 depending on testing goals and requirements.

According to an aspect of the invention, if the suite of instruments (comprising component detection system 24) used to monitor vehicle exhaust emissions is too sensitive for a particular testing application, or if the dilution of the vehicle exhaust emissions is too small to ensure that water vapor is not condensed, or that excess particles are not formed, or if other difficulties are encountered; a number of modifications may be implemented. For example, the extraction air flow (generated by flow generator 22) may be increased with a larger turbine and, if it is desirable to maintain the same linear flow rates, a larger diameter collector 18 (or extraction tube) may be used, and/or the position of delivery portion 18b may be moved closer to the upstream end of gathering structure 20 (e.g., closer to first location 42). In this configuration, with the same vehicle (and with reference to the non-limiting example discussed above), an exhaust plume which might have, for example, occupied two seconds previously may now occupy sixteen seconds because a first exhaust sample (at first location 42) arrives more or less immediately at component detection system 24, while the last exhaust sample (emitted at or near second location 44) occurs approximately eight seconds later and takes approximately eight more seconds to travel back down extraction portion 18a to delivery portion 18b and ultimately to component detection system 24.

Figure 3:
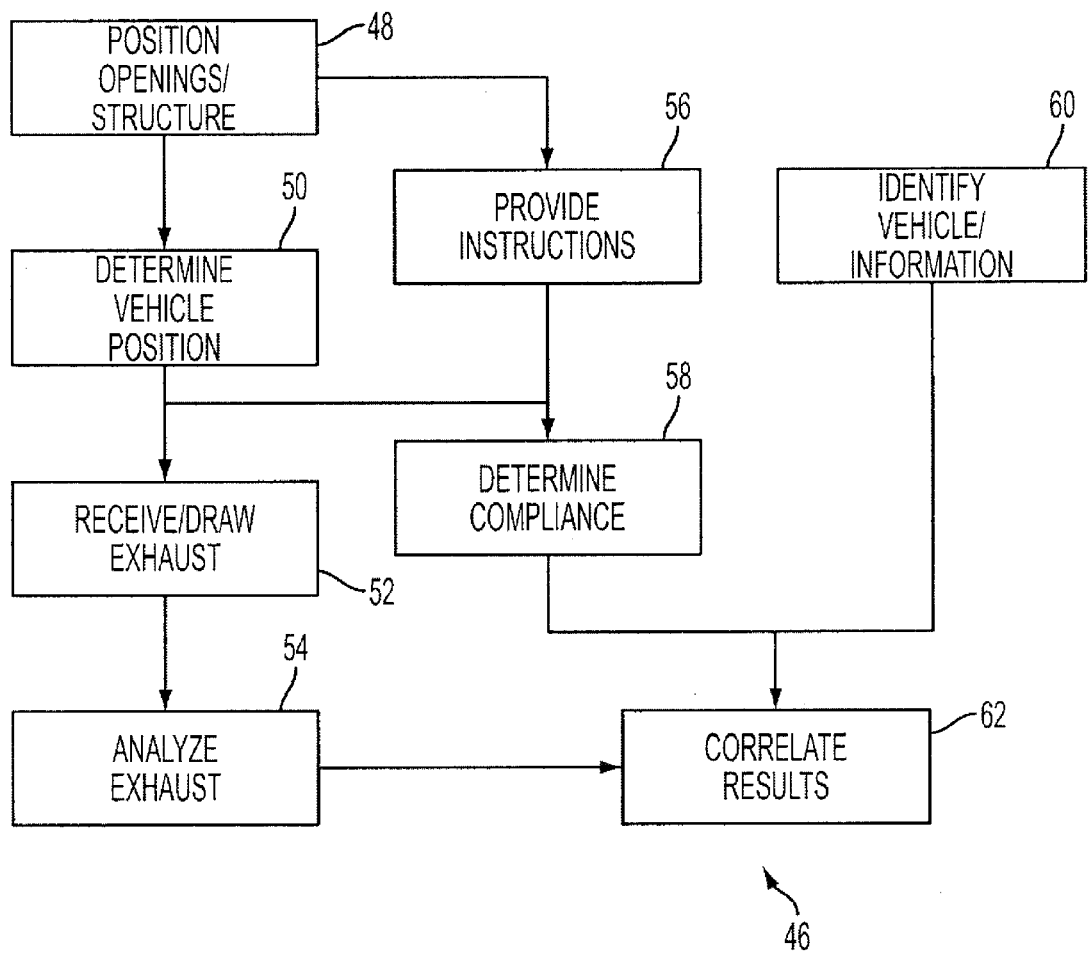
FIG. 3 illustrates a method of quantifying the presence of one or more components in an exhaust plume of a vehicle traveling on a roadway, in accordance with one or more implementations of the invention.

FIG. 3 illustrates a method 46 of quantifying the presence of one or more components in an exhaust plume of a vehicle traveling on a roadway, in accordance with one or more implementations of the invention. Although some of the operations of method 46 are discussed below with respect to the components of system 10 described above and illustrated in FIGS. 1-2, it should be appreciated that this is for illustrative purposes only, and that method 46 may be implemented with alternative components and/or systems without departing from the scope of this disclosure. Further, the particular arrangement of the operations illustrated in FIG. 3 and described hereafter is not intended to be limiting. In some implementations, various ones of the operations could be performed in an order other than the one set forth, various ones of the operations may be combined with others and/or be omitted altogether, and/or various additional operations may be added without departing from the scope of the disclosure, as should be appreciated.

At an operation 48, one or more openings of a collector and/or a gathering structure may be positioned above the surface of the roadway such that one or more surfaces of the gathering structure may cause exhaust emitted by the vehicle as it travels on the roadway to gather around the one or more openings of the collector. In some implementations, the collector and/or the gathering structure may be similar to or the same as collector 18 and/or gathering structure 20, shown in FIGS. 1-2 and described above.

At an operation 50, information related to the position of the vehicle is determined. The information related to the position of the vehicle may include one or more of the position, speed, acceleration, and/or jerk of the vehicle. The information determined at operation 50 may include one or both of information related to the position of the vehicle with respect to the gathering structure and/or collector openings positioned at operation 48, and/or the operating conditions under which the vehicle is operating while it is adjacent to the gathering structure and/or collector openings. In some implementations, operation 50 may be performed by a position tracking system that is the same as or similar to position tracking system 30, shown in FIGS. 1-2 and described above.

At an operation 52, exhaust emitted by the vehicle may be received into the plurality of collector openings. Receiving the exhaust into the plurality of collector openings may include generating a flow of air from the collector openings into the collector that draws the exhaust into the collector by way of the collector openings. The flow of air may be created via suction within the collector. In some instances, the generation of the flow of air may be triggered by a determination of the position of the vehicle at operation 50 (e.g., that the vehicle is at or approaching the gathering structure and/or collector openings). In some implementations, the flow of air may be generated by a flow generator that is the same as or similar to flow generator 22, shown in FIGS. 1-2 and described above.

At an operation 54, exhaust received into the collector openings at operation 52 may be analyzed to quantify the presence of one or more components in the received exhaust. The exhaust may be delivered from the collector openings to a component detection system by the flow of air generated at operation 52, and the component detection system may perform the analysis of the received exhaust at operation 54. In some instances, the analysis of the presence of components in air received at operation 52 into the collector openings may be triggered by a determination of the position of the vehicle at operation 50 (e.g., that the vehicle is at or approaching the gathering structure and/or collector openings). In some implementations, the component detection system may include a component detection system that is the same as or similar to component detection system 24, shown in FIGS. 1-2 and described above.

At an operation 56, instructions may be provided to the vehicle that dictate the manner in which the vehicle should be operated when it is adjacent to the gathering structure and/or collector openings positioned at operation 48. In some instances, the instructions may be dynamic (e.g., delivered via an electronic display and/or speaker. In some instances, the instructions may be static (e.g., delivered via signage). In some implementations, operation 56 may be performed by a vehicle communication system that is the same as or similar to vehicle communication system 28, shown in FIGS. 1-2 and described above.

At an operation 58, compliance of the vehicle with the instructions provided to the vehicle at operation 56. The compliance of the vehicle with the provided instructions may be based on information related to the position, speed, acceleration, and/or jerk of the vehicle determined at operation 50. In some implementations, operation 58 may be performed by a computer that is similar to or the same as computer 26, shown in FIGS. 1-2 and described above.

At an operation 60, the vehicle and/or vehicle information related to the vehicle (e.g., owner information, driver information, license information, make, model type, model year, etc.) may be identified. In some implementations, operation 60 may be performed by a vehicle identification system that is the same as or similar to vehicle identification system 32, shown in FIGS. 1-2 and described above.

At an operation 62, results of the analysis performed at operation 54 may be correlated with one or both of compliance information determined at operation 58 and/or vehicle information identified at operation 60. This may create a record that relates results of the analysis with the appropriate vehicle (and/or class of vehicle), and/or specifies at least some of the parameters under which testing was conducted (e.g., whether the vehicle complied with the instructions provided at operation 58 during the testing).

Figure 4:
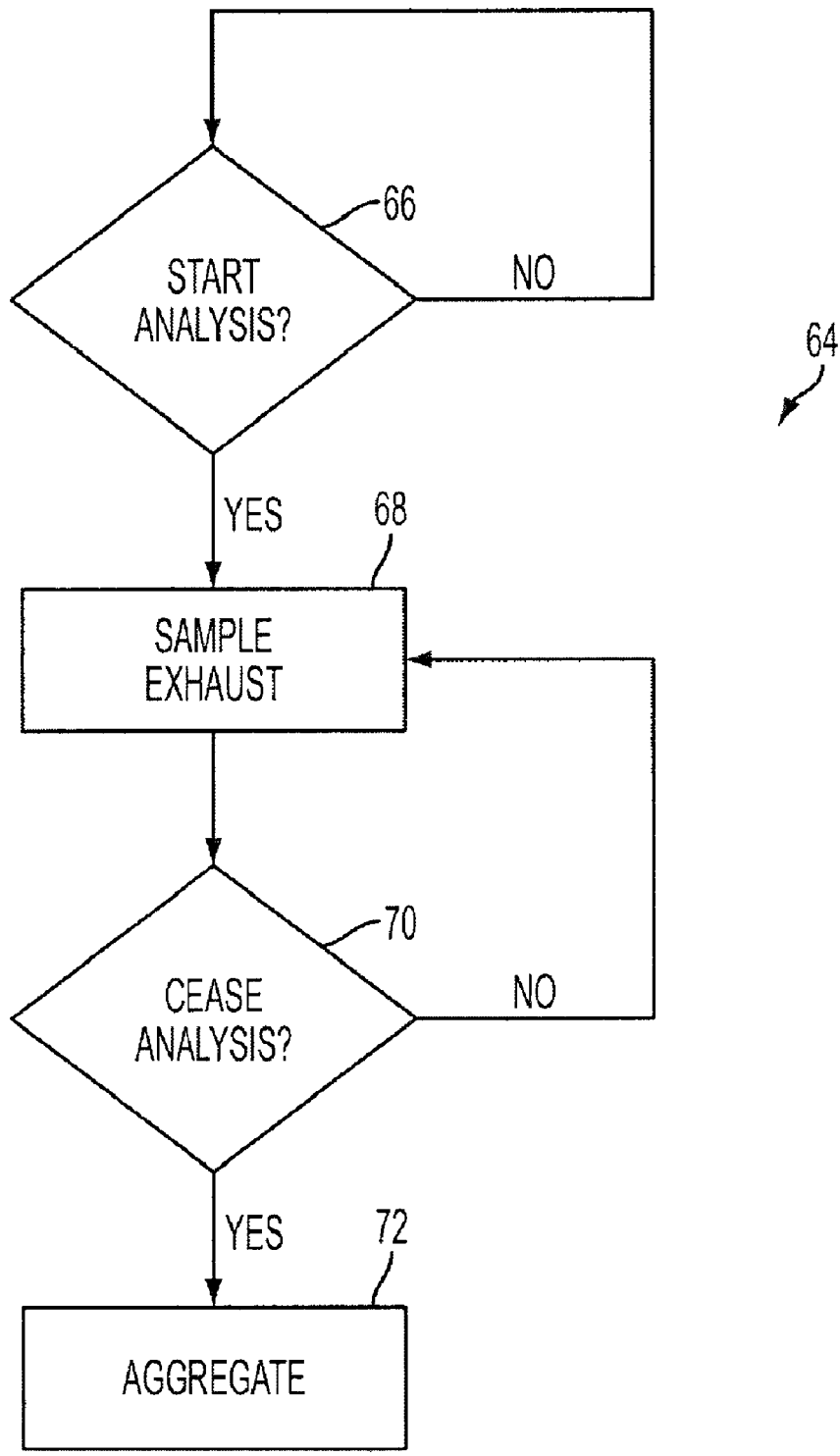
FIG. 4 illustrates a method of analyzing exhaust to quantify the presence of one or more components in the exhaust, according to one or more implementations of the invention.

FIG. 4 illustrates a method 64 of analyzing exhaust to quantify the presence of one or more components in the exhaust, according to one or more implementations of the invention. In the description of method 64 and one or more of its operations below, specific reference is made to various components shown in FIGS. 1-2 and described above and/or various operations shown in FIG. 3 and described above. However, this should not be viewed as limiting. Instead, method 64 should be appreciated as being usable with a variety of different systems and methods. Further, the particular arrangement of the operations of method 64 illustrated in FIG. 4 and described hereafter is not intended to be limiting. In some implementations, various ones of the operations could be performed in an order other than the one set forth (or concomitantly with other ones of the operations), various ones of the operations may be combined with others and/or be omitted altogether, and/or various additional operations may be added without departing from the scope of the disclosure, as should be appreciated.

At an operation 66, a determination may be made as to whether analysis of the exhaust should begin (or has begun). Operation 66 may include determining whether exhaust received into collector openings adjacent to a roadway along which a vehicle is traveling has reached a component detection system performing the analysis. For example, operation 66 may include determining whether exhaust received at operation 52 of method 46, shown in FIG. 3 and described above, has reached the component detection system. The determination made at operation 66 may be based on a position of the vehicle (e.g., at operation 50 of method 46) and/or a known delay time between the reception of the exhaust into the collector openings and the arrival of the received exhaust at the component detection system. In some implementations, operation 66 may be performed by a computer that is the same as or similar to computer 26, shown in FIGS. 1-2 and described above.

If the determination is made at operation 66 that analysis of the exhaust should not (or has not) begun, method 64 performs operation 66 yet again. If the determination is made at operation 66 that analysis of the exhaust should begin, then method 64 proceeds to an operation 68, at which the exhaust is sampled to quantify the presence of one or more components. In some instances, this may include taking a single measurement of the one or more components and proceeding to an operation 70. In some instances, this may include taking a series of samples at a predetermined sampling interval and then proceeding to operation 70. In some implementations, operation 68 may be performed by a component detection system that is the same as or similar to component detection system 24, shown in FIGS. 1-2 and described above.

At operation 70, a determination may be made as to whether analysis of the exhaust should cease (or has ceased). Operation 70 may include determining whether exhaust received into collector openings adjacent to a roadway along which a vehicle is traveling is no longer reaching component detection system performing the analysis (e.g., because the vehicle has passed the collector openings). For example, operation 70 may include determining whether all of the exhaust received at operation 52 of method 46, shown in FIG. 3 and described above, has already been sampled and exhausted by the component detection system. The determination made at operation 70 may be based on a position of the vehicle (e.g., at operation 50 of method 46) and/or a known delay time between the reception of the exhaust into the collector openings and the arrival of the received exhaust at the component detection system. In some implementations, operation 70 may be performed by a computer that is the same as or similar to computer 26, shown in FIGS. 1-2 and described above.

If the determination is made at operation 70 that analysis of the exhaust should not cease (or has not ceased), method 64 may return to operation 68. If the determination is made at operation 70 that analysis of the exhaust should cease (or has ceased), then method 64 may proceed to an operation 72.

At operation 72, the samples quantifying the presence of the one or more components in the exhaust, taken at operation 68, are aggregated by one or more of several possible mathematical techniques to provide an aggregate quantification of the presence of the one or more components in the exhaust of the vehicle. In some instances, operation 72 may include averaging the samples. In some implementations, operation 72 may be performed by a computer that is the same as or similar to computer 26, shown in FIGS. 1-2 and described above.

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any implementation can be combined with one or more features of any other implementation.

Figure 5:
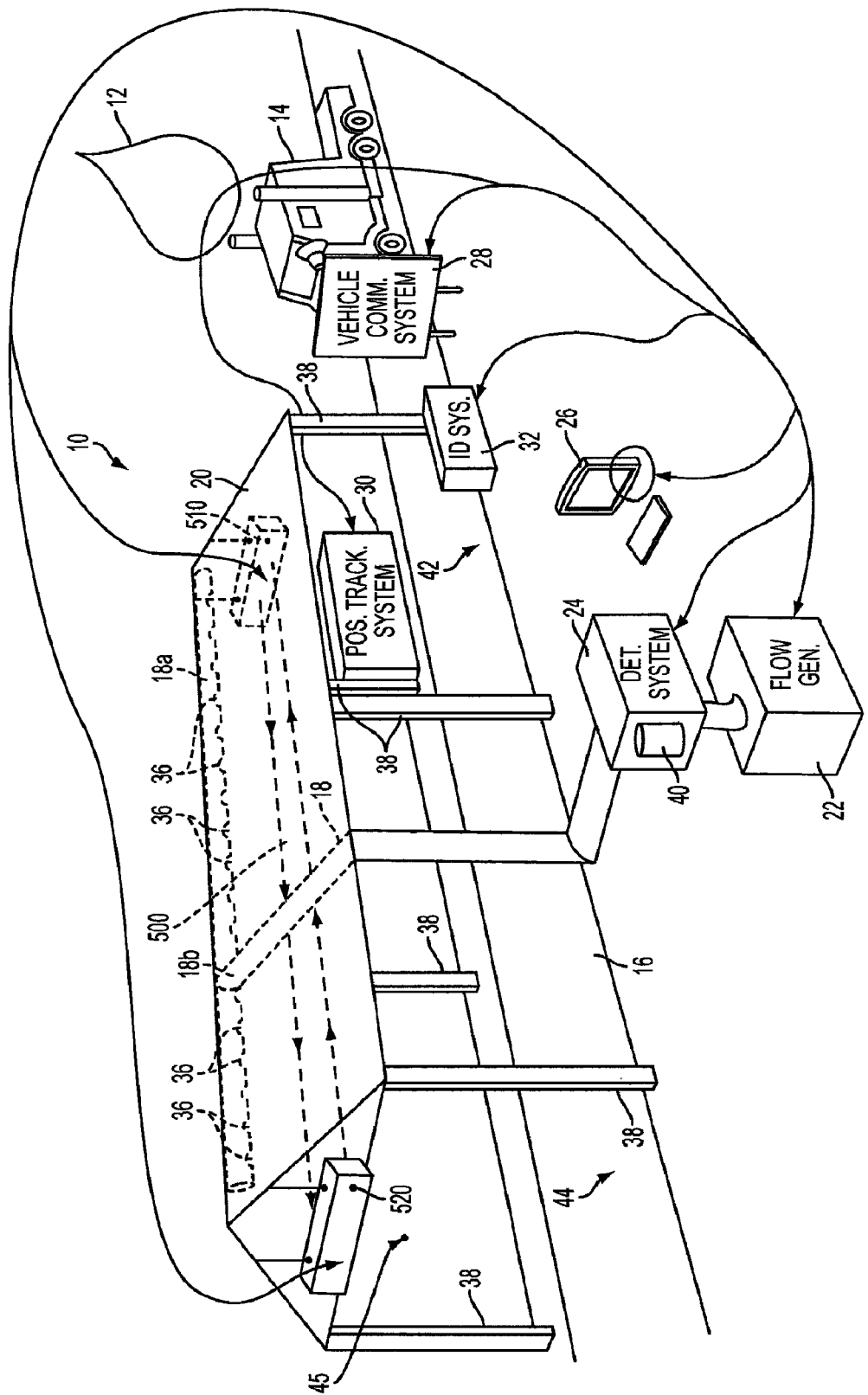
FIG. 5 illustrates a system for analyzing an exhaust plume of a vehicle traveling on a roadway, according to one or more implementations of the invention.

In one alternative implementation, and with reference to FIG. 5, system 10 may further comprise a remote emissions sensing ("RES") system that may be used in lieu of, or in addition to, the extractive sampling system described in detail above.

The RES system may be configured to measure emissions in exhaust plume 12 (of vehicle 14) in an optical measurement path 500 that runs in a direction substantially parallel to extraction portion 18*a* of collector 18 (or, in other words, in a direction substantially parallel to a direction of travel of vehicle 14 on roadway 16). In this regard, exhaust emitted by vehicle 14 may be directed by gathering structure to an elevated position above roadway 16 such that the exhaust is present in optical measurement path 500.

In one implementation, the RES system may comprise a source/detector unit 510 positioned at or near first location 42 (e.g., at a first end or entrance to gathering structure 20). The source/detector unit 510 may be provided at an elevated position above roadway 16 (e.g., hung from the roof of gathering structure 20).

Source/detector unit 510 may comprise one or more sources of electromagnetic radiation (ER) which may be used in the absorption spectroscopy measurement of various components of vehicle exhaust emissions in a known manner. The source may comprise an infrared (IR) radiation source. In alternative implementations, other types of radiation sources may be used including, for example, an ultraviolet (UV) source, a visible light source, or other suitable sources as known and understood by those having skill in the art. In some implementations, a combination of radiation sources may be used.

Source/detector unit 510 may further comprise one or more detectors or a detector array for detecting radiation in a known manner. A detector array may be chosen to permit detection of electromagnetic radiation emitted by the source. For example, the detector array may comprise a photodetector (e.g., a photodiode), a photomultiplier tube (PMT), a spectrometer, or any other suitable radiation detector. In one implementation, a mercury cadmium telluride (Hg—Cd—Te) photodetector may be used to detect IR radiation. Other suitable detectors or detector arrays or combinations thereof may also be used. In one implementation, a single detector with multiple filters may be used instead of an array employing multiple detectors. The multiple filters may be moveable, such as spinning filters, to allow multiple components to be detected. In this regard, a single detector can be employed to detect a plurality of different exhaust components because each of the moveable filters is designed to allow only the wavelength band of interest by a particular exhaust component to pass to the detector. According to yet another implementation, the RES system may comprise a spectrometer, or other detecting device which may be used to detect more than one component.

In one implementation, the RES system may comprise transfer optics 520 mounted in a manner to allow radiation from the source of source/detector unit 510 to be reflected back to the detector array of source/detector unit 510 along measurement path 500 for analysis. Transfer optics 520 may be positioned at or near second location 44 (e.g., at a second end or exit from gathering structure 20). Transfer optics 520 may be provided at an elevated position above roadway 16 (e.g., hung from the roof of gathering structure 20) and aligned with source/detector unit 510. Transfer optics 520 may comprise a mirror, flat mirror, lateral transfer mirror (LTM), vertical transfer mirror (VIM), retroflector, or other device. In one implementation, transfer optics 520 may comprise a lateral transfer mirror to reflect radiation from the source along a path displaced laterally or vertically, depending on orientation, from the incident direction. Other configurations may be implemented.

In some implementations, the position of source/detector unit 510 and transfer optics 520 may be reversed such that source/detector unit 510 may be positioned at or near second location 44 (e.g., at a second end or exit from gathering structure 20), while transfer optics 520 may be positioned at a first location 42 (e.g., at a first end or entrance to gathering structure 20).

Additionally, in other implementations (not illustrated), source/detector unit 510 may be replaced with a unit that includes a source, while transfer optics 520 may be replaced with a unit that includes a detector (aligned with the source). In this implementation, a beam of radiation makes one pass along measurement path 500 (i.e., from the source to the detector) rather than two passes along measurement path as shown in FIG. 5 (from source/detector unit 510 to transfer optics 520 and then back to source/detector unit 510). Of course, in some implementations, transfer optics 520 may be replaced with a unit that includes a source, and source/detector unit 510 may be replaced with a unit that includes a detector (aligned with the source). Other configurations may be implemented.

According to an aspect of the invention, source/detector unit 510, transfer optics 520, and/or other components of the RES system may be in operative communication with one or more of the other components of system 10 (described in detail above) including, for example, computer 26, vehicle communication system 28, position tracking system 30, vehicle identification system 32, and/or other components.

Computer 26 may execute one or more software applications to calculate the relative amounts of various exhaust gas constituents, concentrations of various exhaust gas constituents (e.g., HC, $CO_2$, $NO_x$, CO, etc.), the decay rate (e.g., dissipation in time) of the exhaust constituents, the opacity of an exhaust plume, the temperature, speed and acceleration of the vehicle, and to determine other desirable information as well.

In one implementation, computer 26 may calculate the relative amounts of various exhaust gas constituents by computing the ratio of the absorption for a particular exhaust gas constituent to the $CO_2$ gas constituent. For example, in one implementation, the source (of source/detector unit 510) may be configured to pass a beam of EM radiation through exhaust plume 12 (present in optical measurement path 500) of vehicle 14 as vehicle 14 passes through gathering structure 20. The beam may be directed by transfer optics 520 back to the detector (or detector array) of source/detector unit 510. One or more filters (not illustrated) may be associated with the detector array to the enable detector array to determine the intensity of EM radiation having a particular wavelength or range of wavelengths. The wavelengths may be selected to correspond to wavelengths absorbed by molecular species of interest in an exhaust plume (e.g., hydrocarbons (HC), carbon monoxide (CO), carbon dioxide ($CO_2$) and nitrogen oxides ($NO_x$) such as NO and $NO_2$). One or more detector output voltages represent the intensity of the EM radiation measured by that detector.

These voltages are then input to computer 26. Computer 26 may calculate the difference between the known intensity of the source and the intensity detected by the detectors to determine the amount of absorption by the particular molecular species (based on predetermined wavelengths associated with that species). Based on the measured absorption(s), the number of molecules in the measurement path of one or more molecular species in the emissions may be determined in a known manner.

Calibration of the RES system may be enabled by a calibration cell (not illustrated), or through puff calibration (via a calibration gas canister), as known in the art.

As noted above, the RES system may be used independently, or in addition to the extractive sampling system (e.g., collector 18, gathering structure 20, flow generator 22, component detection system 24, etc.) described in detail above.

For example, in one implementation, gaseous pollutants in vehicle exhaust emissions may be monitored optically (via the RES system) while various parameters of smoke, such as black carbon content or size distribution, may be monitored using the extractive sampling system. Of course, in one implementation, smoke may be measured optically via the RES system as described in, for example, U.S. Pat. No. 6,701,056, which is hereby incorporated herein by reference in its entirety.

In an alternative implementation, similar measurements may be made by both the RES system and the extractive sampling system for data validation or comparison purposes.

Other implementations, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A system configured to be positioned at a site along a roadway, and to determine the concentration of one or more constituents present in a sample of exhaust emissions emitted by a vehicle traveling on the roadway from a first location on the roadway to a second location on the roadway, the system comprising:
   a component detection system configured to determine the concentration of one or more constituents present in vehicle exhaust emissions;
   a collector operatively coupled to the component detection system, wherein the collector is positioned above the surface of the roadway and has one or more openings for receiving the exhaust emissions of the vehicle to be analyzed by the component detection system;
   a gathering structure having one or more surfaces positioned to direct the exhaust emissions of the vehicle to be analyzed by the component detection system to the one or more openings of the collector prior to measurement by the component detection system;
   wherein the component detection system is configured to receive a sample of the exhaust emissions of the vehicle via the collector, and to determine the concentration of one or more constituents present in the sample of exhaust emissions; and
   wherein the collector is configured such that collection times for exhaust emissions emitted by the vehicle to be conveyed through the collector to the component detection system vary as a function of position of the one or more openings of the collector along the roadway between the first location and the second location to aggregate the exhaust emissions for detection within the component detection system.

2. The system of claim 1, wherein the roadway comprises a test lane.

3. The system of claim 1, wherein the gathering structure comprises a roof that is supported above the surface of the roadway by one or more supports such that the vehicle can pass under the roof while traveling along the roadway.

4. The system of claim 1, wherein the roadway comprises a single vehicle travel lane, and wherein the roof of the gathering structure covers the single vehicle travel lane.

5. The system of claim 1, wherein the collector comprises:
   an extraction portion which runs parallel to a direction of travel of the roadway, with the one or more openings being formed therein; and
   a delivery portion configured to convey exhaust emissions extracted by the extraction portion through the one or more openings toward the component detection system, wherein the location at which the delivery portion interfaces with the extraction portion facilitates aggregation of the exhaust emissions at the interface.

6. The system of claim 5, wherein the extraction portion interfaces with the delivery portion at or near an end of the extraction portion that is located nearest the second location.

7. The system of claim 5, wherein the extraction portion comprises a perforated lumen.

8. The system of claim 7, wherein one or more of a size, shape, or distribution of the perforations permit freer flow into the extraction portion of the collector for locations that are closer to the first location.

9. The system of claim 1, wherein the collector is fastened to an underside of the roof of the gathering structure such that the one or more openings of the collector face the surface of the roadway.

10. The system of claim 1, wherein the gathering structure further comprises:
    a roof that is supported above the surface of the roadway by one or more supports such that the vehicle can pass under the roof while traveling along the roadway; and
    an apron that extends from the roof toward the surface of the roadway on a first side of the roadway, and further extends parallel to a direction of travel on the roadway, wherein the apron is configured to direct exhaust emissions, emitted by a vehicle outward in a direction toward the first side of the roadway, toward the one or more openings of the collector.

11. A method of determining the concentration of one or more constituents present in a sample of exhaust emissions emitted by a vehicle traveling on a roadway from a first location to a second location, the method comprising:
    directing the exhaust emissions of the vehicle to be analyzed by a component detection system to one or more openings of a collector, prior to measurement by the component detection system, via one or more surfaces of a gathering structure, wherein the collector is positioned above the surface of the roadway;
    drawing exhaust emissions received in the one or more openings of the collector to the component detection system via suction, wherein the collector is configured such that collection times for exhaust emissions drawn through the one or more openings of the collector to the component detection system vary as a function of position of the one or more openings of the collector along the roadway between the first location and the second location to aggregate the exhaust emissions for detection within the component detection system.

12. The method of claim 11, wherein the roadway comprises a test lane.

13. The method of claim 11, wherein the gathering structure comprises a roof that is supported above the surface of the roadway by one or more supports such that the vehicle can pass under the roof while traveling along the roadway.

14. The system of claim 11, wherein the roadway comprises a single vehicle travel lane, and wherein the roof of the gathering structure covers the single vehicle travel lane.

15. The method of claim 11, wherein the collector comprises:
    an extraction portion which runs parallel to a direction of travel of the roadway, with the one or more openings being formed therein; and
    a delivery portion configured to convey exhaust emissions extracted by the extraction portion through the one or more openings toward the component detection system, wherein the location at which the delivery portion interfaces with the extraction portion facilitates aggregation of the exhaust emissions at the interface.

16. The method of claim 15, wherein the extraction portion interfaces with the delivery portion at or near an end of the extraction portion that is located nearest the second location.

17. The method of claim 15, wherein the extraction portion comprises a perforated lumen.

18. The method of claim 17, wherein one or more of a size, shape, and/or distribution of the perforations permit freer flow into the extraction portion for locations that are closer to the first location.

19. The method of claim 11, wherein the collector is fastened to an underside of the roof of the gathering structure such that the one or more openings of the collector face the surface of the roadway.

20. The method of claim 11, wherein the gathering structure further comprises a roof that is supported above the surface of the roadway by one or more supports such that the vehicle can pass under the roof while traveling along the roadway; and an apron that extends from the roof toward the surface of the roadway on a first side of the roadway, and further extends parallel to a direction of travel on the roadway, wherein the apron is configured to direct exhaust emissions, emitted by a vehicle outward in a direction toward the first side of the roadway, toward the one or more openings of the collector.

21. A system configured to be positioned at a site along a roadway, and to determine the concentration of one or more constituents present in a sample of exhaust emissions emitted by a vehicle traveling on the roadway, the system comprising:

a gathering structure having a first end, a second end, and a roof having a length that extends from the first end of the gathering structure to the second of the gathering structure in a direction substantially parallel to a direction of travel of the roadway, wherein the roof of the gathering structure is supported above the surface of the roadway by one or more supports and pools exhaust emissions emitted by the vehicle as the vehicle passes under the roof while traveling on the roadway;

at least one radiation source disposed on a underside of the roof of the gathering structure proximate to the first end of the gathering structure, the radiation source configured to emit a radiation beam along an optical measurement path, wherein the optical measurement path extends in a direction substantially parallel to a direction of travel of the roadway and along an underside of the roof so as to pass through the exhaust emissions of the vehicle pooled by the gathering structure;

at least one radiation detector configured to receive the radiation beam and generate at least one signal indicative of the radiation absorption of first and second vehicle exhaust constituents in first and second wavelength bands; and a computer configured to receive the at least one signal and calculate a ratio of the radiation absorption of the first vehicle exhaust constituent to the radiation absorption of the second vehicle exhaust constituent.

22. The system of claim 21, wherein the at least one radiation detector is disposed on a underside of the roof of the gathering structure proximate to the second end of the gathering structure such that the radiation beam makes a single pass along the optical measurement path from the at least one radiation source, through the exhaust emissions of the vehicle pooled by the gathering structure, to the at least one radiation detector.

23. The system of claim 21, wherein the at least one radiation detector is disposed on a underside of the roof of the gathering structure proximate to the first end of the gathering structure and adjacent to the at least one radiation source, the system further comprising:

optics disposed on a underside of the roof of the gathering structure proximate to the second end of the gathering structure, the optics configured to reflect the radiation beam emitted by the at least one radiation source back along the optical measurement path to the at least one radiation detector such that the radiation beam makes at least two passes through the exhaust emissions of the vehicle pooled by the gathering structure.

24. The system of claim 21, wherein the first vehicle exhaust constituent comprises one of CO, HC, or NO.

25. The system of claim 21, wherein the second vehicle exhaust constituent comprises carbon dioxide ($CO_2$).

* * * * *